United States Patent
Bendriem et al.

(10) Patent No.: US 8,634,624 B2
(45) Date of Patent: Jan. 21, 2014

(54) METHOD AND APPARATUS FOR GENERATING AN IMAGE FROM MEDICAL IMAGE DATA

(75) Inventors: Bernard Bendriem, Knoxville, TN (US); Timor Kadir, Oxford (GB); Matthew David Kelly, Botley (GB); Guenther Platsch, Roethenbach (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 893 days.

(21) Appl. No.: 12/760,645

(22) Filed: Apr. 15, 2010

(65) Prior Publication Data

US 2010/0290684 A1    Nov. 18, 2010

(30) Foreign Application Priority Data

Apr. 15, 2009   (GB) .................................. 0906461.9

(51) Int. Cl.
*G06K 9/00*   (2006.01)

(52) U.S. Cl.
USPC ........... 382/131; 382/260; 382/128; 382/103; 600/407; 378/4

(58) Field of Classification Search
USPC ........... 382/128, 103, 131; 348/340; 600/407; 378/4
See application file for complete search history.

(56) References Cited

U.S. PATENT DOCUMENTS

| | | | |
|---|---|---|---|
| 6,529,758 B2* | 3/2003 | Shahidi ........................ | 600/407 |
| 6,829,323 B2* | 12/2004 | Toth et al. ........................ | 378/4 |
| 7,031,504 B1* | 4/2006 | Argiro et al. ................... | 382/131 |
| 7,257,244 B2* | 8/2007 | Miga ............................. | 382/128 |
| 7,356,174 B2* | 4/2008 | Leue et al. ..................... | 382/131 |
| 7,853,041 B2* | 12/2010 | Shamaie ....................... | 382/103 |
| 8,111,889 B2* | 2/2012 | Basu et al. .................... | 382/131 |
| 8,335,358 B2* | 12/2012 | Kalke ........................... | 382/128 |
| 2005/0254721 A1* | 11/2005 | Hagiwara ...................... | 382/260 |
| 2008/0211956 A1* | 9/2008 | Imada et al. ................... | 348/340 |

OTHER PUBLICATIONS

Google patents search, Feb. 14, 2013.*
Google patents search, Feb. 16, 2013.*
Google patents search, Feb. 25, 2013.*
Google patents search, Sep. 9, 2013.*
"Partial-Volume Effect in PET Tumor Imaging," Sorel et al, The Journal of Nuclear Medicine, vol. 48, No. 6 (2007) pp. 932-945.
"Post-Reconstruction Filtering of Positron Emission Tomography Whole-Body Emission Images and Attenuation Maps Using Nonlinear Diffusion Filtering," Demirkaya, Academic Radiology, vol. 11, No. 10 (2004) pp. 1105-1114.
"Detailed Investigation of Transmission and Emission Data Smoothing Protocols and Their Effects on Emission Images," Chatziioannou et al, IEEE Trans. on Nuclear Science, vol. 43, Issue 1 (1996), (abstract).

(Continued)

*Primary Examiner* — Dilek B Cobanoglu
(74) *Attorney, Agent, or Firm* — Schiff Hardin LLP

(57) ABSTRACT

In a methods and apparatus for generating an image for display from medical image data of a subject, image data is processed to reconstruct a pre-image data set, and a filter applied to the pre-image data set to produce a filtered image for display, while a value of a variable is obtained from the pre-image data set, for display with the filtered image. The value obtained from the pre-image data can be used for quantification of a feature of the medical image data.

14 Claims, 3 Drawing Sheets

(56) References Cited

OTHER PUBLICATIONS

"Correction for Partial Volume Effects in PET: Principle and Validation," Rousset et al., The Journal of Nuclear Medicine, vol. 39, No. 5 (1998), pp. 904-911.

"Partial-Volume Correction in PET: Validation of an Iterative Postreconstruction Method with Phantom and Patient Data," Teo et al., The Journal of Nuclear Medicine, vol. 48, No. 5 (2007), pp. 802-810.

"Evaluation of anatomy based reconstruction for partial volume correction in brain FDG-PET," Beete et al., NeuroImage, vol. 23 (2004), pp. 305-317.

* cited by examiner

METHOD AND APPARATUS FOR GENERATING AN IMAGE FROM MEDICAL IMAGE DATA

BACKGROUND OF THE INVENTION

1. Field of the Invention

The present invention is directed to a method and apparatus for generating an image for display from medical image data of a subject.

2. Description of the Prior Art

In the medical imaging field, several imaging schemes are known. For example PET (Positron Emission Tomography) is a method for imaging a subject in 3D using an injected radioactive substance which is processed in the body, typically resulting in an image indicating one or more biological functions.

A key criterion used in evaluating suspicious lesions in a PET scan is the Standardized Uptake Value (SUV). This value is computed from the number of counts of emission events recorded per voxel in the image reconstructed from the event data captured in the PET scan (coincidence emission events along the line of response). Effectively the SUV's purpose is to provide a standardized measure of the spatial distribution of radiotracer concentration throughout the imaged portion of the body.

Partial volume effect (PVE) in PET is due to a combination of the finite spatial resolution of the scanner and image sampling. It results in under-estimation of the true activity for small lesions (or any hot region against a cold background). The effect is typically apparent for lesions smaller than three times the full width at half maximum (FWHM) of the reconstructed image resolution.

The magnitude of this effect on mean SUV for a typical PET scanner is shown in the table below (Table 1), where the recovery coefficient is the percentage of the true lesion-to-background ratio measured in the reconstructed image. The table lists typical recovery coefficients for spherical lesions with a 4:1 lesion-to-background activity concentration ratio. These values were obtained from a NEMA Image Quality phantom scanned on a Siemens Biograph Scanner and reconstructed using OSEM with a 5 mm FWHM post filter.

TABLE 1

| Lesion diameter | Recovery coefficient |
| --- | --- |
| 10 mm | 22.5% |
| 13 mm | 39.4% |
| 17 mm | 55.1% |
| 22 mm | 71.7% |

While no approach to partial volume correction (PVC) is currently available clinically, a number of approaches have been proposed. Soret et al. ((2007) Partial volume effect in PET tumor imaging, JNM. 48(6); 932-944.) provides a comprehensive review of these methods. In brief, these methods can be broadly classified into three groups:

1. Those using anatomical information from higher resolution imaging modalities to correct for spill-over and tissue-fraction effects (e.g., the GTM method by Rousset et al. ((1998) Correction for partial volume effects in PET: principle and validation, JNM. 39; 904-9111998));

2. Those using iterative deconvolution to correct for the point spread function (PSF) of the system (e.g., Teo et al. ((2007) Partial volume correction in PET: validation of an iterative post reconstruction method with phantom and patient data, JNM. 48; 802-810));

3. Those using predetermined recovery coefficients as measured from phantom acquisitions (e.g., in the form of a look up table).

With the exception of one approach by Baete et al. ((2004) Evaluation of anatomy based reconstruction for partial volume correction in brain FDG-PET, NeuroImage. 23; 305-317), which falls into the first group above, each of these methods takes the fully reconstructed image as input.

Methods from groups 1 and 3 require significant user input prior to correction of PVE, and are heavily dependent on the quality of the segmentation and registration necessary for performing the correction.

Methods from group 2 require little user intervention on top of the usual definition of the region of interest (ROI) for quantification. However, they require an accurate approximation of the PSF of the system.

SUMMARY OF THE INVENTION

An object of the present invention is to address these problems and provide improvements upon the known devices and methods.

In general terms, one embodiment of a first aspect of the invention is a method of generating an image for display from medical image data of a subject, including processing the image data to reconstruct a pre-image data set, applying a filter to the pre-image data set to produce a filtered image for display, and obtaining from the pre-image data set a value of a variable for display with the filtered image.

This method addresses the problem of partial volume effect by taking a value directly from the image data before the final filter or smoothing stage, and producing it for display with the usual filtered image. This reduces the need for partial volume correction of the final image to produce this value, or for estimating point spread function.

This value obtained from the pre-image data set can therefore be used for quantification (e.g. measurement of mean SUV), alongside the displaying of the normal filtered image for visualization by a clinician.

Preferably, the method includes displaying the value with the filtered image.

Thus the value can be displayed alongside the filtered image, for example overlaid on the filtered image.

Suitably, the step of obtaining the value includes measuring at least one value of the variable for a group of voxel data in the pre-image data set. Preferably, this step includes identifying a user-selected region of interest in the filtered image, determining the group of voxel data from the pre-image data set used to generate this region of interest, and measuring said at least one value from the determined group. In an embodiment, the variable is mean voxel intensity. More preferably, this step comprises setting a minimum size for the region of interest.

In one embodiment, the filter is applied to the pre-image data set at a user workstation. Preferably, the filter is applied on demand for user viewing of the filtered image. Suitably, the method includes, before application of the filter, adding a tag to a header of the pre-image data set to indicate the requirement for a filter.

This allows real-time processing of the pre-image data set at the workstation—the header allows backwards compatibility with other types of workstation.

Preferably, the filter is a smoothing post-filter for reducing image noise.

In general terms, one embodiment of a second aspect of the invention is a method of generating an image for display from medical image data of a subject, including processing the image data to reconstruct a pre-image data set, processing the image data to reconstruct an image data set to produce an image for display, obtaining from the pre-image data set a value of a variable for display with the image, and displaying the value with the image.

Preferably, the step of processing to reconstruct the image data set includes applying a filter to the image data set to produce the image for display.

In general terms, one embodiment of a third aspect of the invention is a workstation apparatus configured to perform a method according to any of the above described aspects and embodiments.

In general terms, one embodiment of a fourth aspect of the invention is an apparatus for generating an image for display from medical image data of a subject, captured by an imaging apparatus. The image-generating apparatus includes a processor configured to process the image data to reconstruct a pre-image data set, apply a filter to the pre-image data set to produce a filtered image for display, and obtain from the pre-image data set a value of a variable for display with the filtered image. The image-generating apparatus also includes and a display device that displays the value with the filtered image.

In general terms, one embodiment of a fifth aspect of the invention also is an apparatus for generating an image for display from medical image data of a subject, captured by an imaging apparatus. In this embodiment the image-generating apparatus includes a processor configured to process the image data to reconstruct a pre-image data set, process the image data to reconstruct an image data set to produce an image for display, and obtain from the pre-image data set a value of a variable for display with the image. The image-generating apparatus also includes a display device that displays the value with the image.

Preferably, the processor is further configured to apply a filter to the image data set to produce the image for display.

In general terms, one embodiment of a sixth aspect of the invention is a computer-readable storage medium encoded with computer program codes that, when the storage medium is loaded into or run on a computer, causes the computer to execute the method, according to any of the above described aspects and embodiments.

DESCRIPTION OF THE PREFERRED EMBODIMENTS

When the following terms are used herein, the accompanying definitions can be applied:

| | |
|---|---|
| FWHM | Full Width and Half Maximum |
| PET | Positron Emission Tomography |
| PSF | Point Spread Function |
| PVC | Partial Volume Correction |
| PVE | Partial Volume Effect |
| ROI | Region Of Interest |
| SUV | Standardized Uptake Value |

Embodiments of the invention can address the previous problems by avoiding the dominant source of PVE introduced by the reconstruction algorithm—namely, the final smoothing filter that is applied post-reconstruction. In standard Biograph TruePoint and non-TruePoint scanners a post-reconstruction smoothing filter is applied to the image before it is transferred to the workstation for review and reading. The size of the filter and hence the degree of smoothing applied may be adjusted but is typically set to the default setting for the type of scan of interest. Kernel sizes from 2-10 mm are typical.

The purpose of the filter is to improve the readability of the scan by reducing the apparent noise, at some expense of the contrast and sharpness. Another effect of the filter is to introduce additional PVE to the image.

Embodiments of the invention therefore reduce the effect of PVE on quantification by modifying the reconstruction workflow such that two images are produced at reconstruction-one for visual reading and the other for quantification. Both can be stored in the database.

An advantage over the prior art is that no additional processing is performed on the image. The invention does not correct for any PVE that arises from any other source other than the post-reconstruction filter and there may be some residual effects. However, experiments shown in Table 1 (above) and Table 2 (below) indicate that the effect is still significant.

Figure 1:
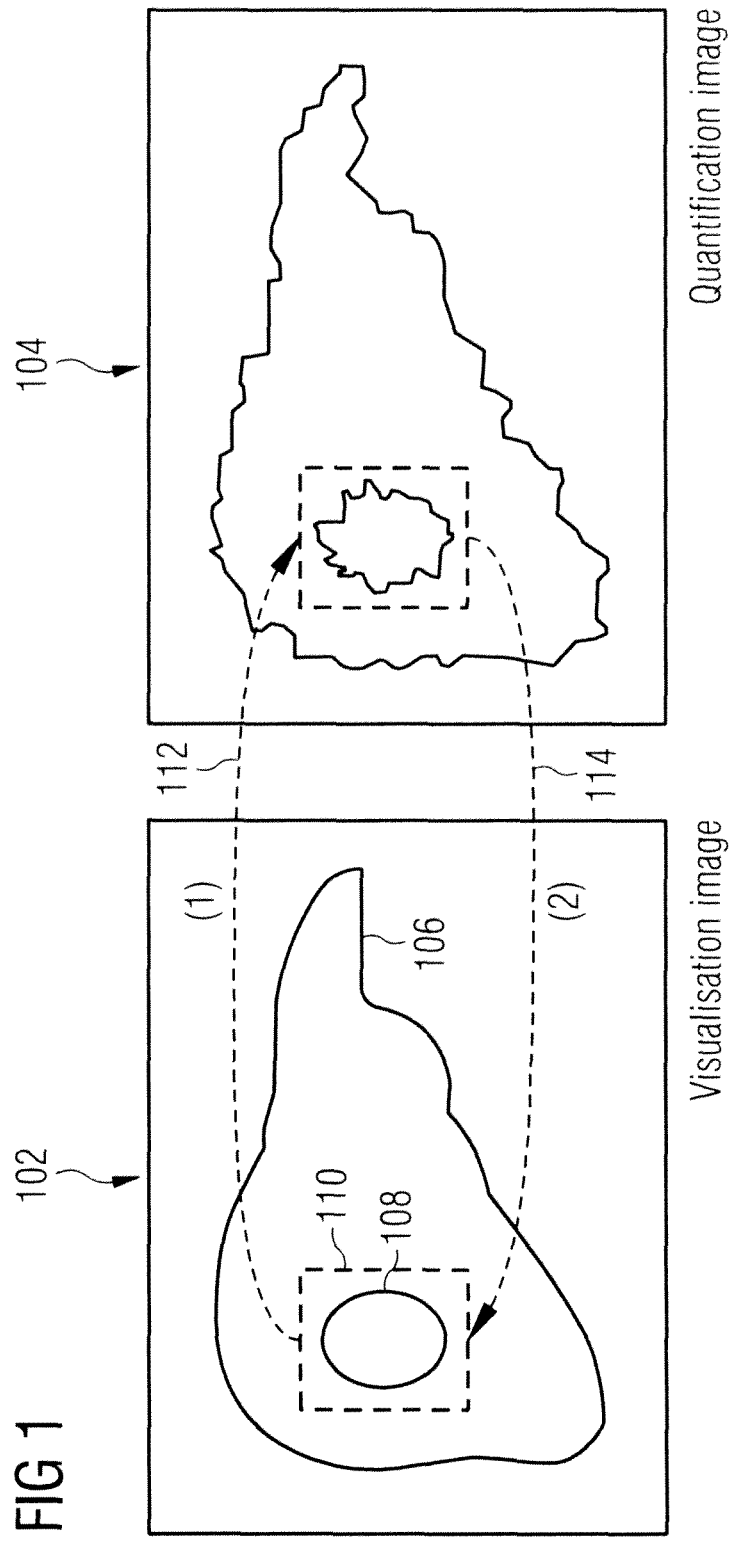
FIG. 1 is a diagram illustrating processing of image data according to an embodiment of the invention.

FIG. 1 is a diagram illustrating the processing and manipulation taking place in an embodiment of the invention. The image data has captured an object 106 for viewing by the clinician. The pre-image data, without the final smoothing filter, has been stored as a quantification image (104). The workstation/viewer presents the visualization image (102) to the user, who uses this image to identify lesions (such as lesion 108) and draw ROIs (such as ROI 110). This ROI 110 is then propagated (112) by the system to the quantification image. Any quantification parameters, such as mean pixel intensity, would then be computed using the data in the quantification image, instead of the viewing/visualization image, and the resultant values propagated (114) back to the viewer for display alongside the visualization image.

Thus, the viewer is allowed the advantages of the visualization image (e.g. better readability), but for quantification has the more robust, more accurate data gathered from the quantification image.

The method of display of the value can be an overlay on the visualization image at the ROI, or a ticker elsewhere on screen, or any similar combination image. Alternatives will be apparent to the those skilled in the art.

The reading workstation can be modified to accept such dual reconstructed images such that the filtered image is displayed to the user and the unfiltered image is used for quantification purposes. Embodiments of the invention may be better suited to ROI quantification, since single voxel values may be too noisy and hence unreliable. A minimal size for the ROI could be defined, which may relate to the size of the kernel used to smooth the visualization image.

Figure 2:
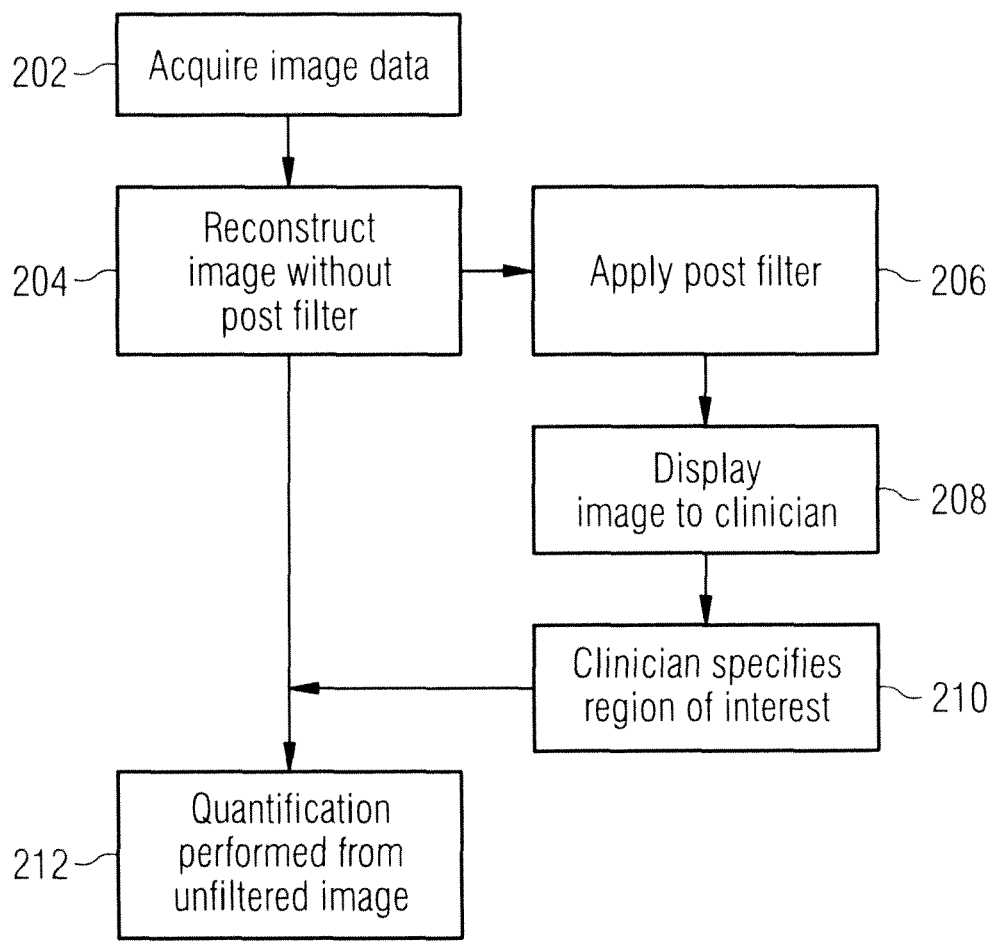
FIG. 2 is a flow diagram illustrating steps in a method according to an embodiment of the invention.

FIG. 2 is a flow diagram illustrating typical steps in an embodiment of the invention. The image data is acquired (202), and the reconstruction performed, but without the final post-filter smoothing (204) to produce the pre-image or quantification data set. This image or data set is then used for quantification (212). In the meantime, the pre-image data/quantification image is also processed with the post filter (206) to provide the separate visualization image, presented to the clinician (208). The clinician chooses an ROI (210), and the values of, for example, mean SUV for the ROI are taken from the quantification image (212).

The post-filtered image may either be created and stored at the time of reconstruction, or applied directly by the viewer at the time of viewing. The various steps may be therefore be shared by separate processing systems or workstations, or may take place at the same workstation, which may provide reconstruction, viewing and propagation of ROIs to the quantification image on the same system.

Figure 3:
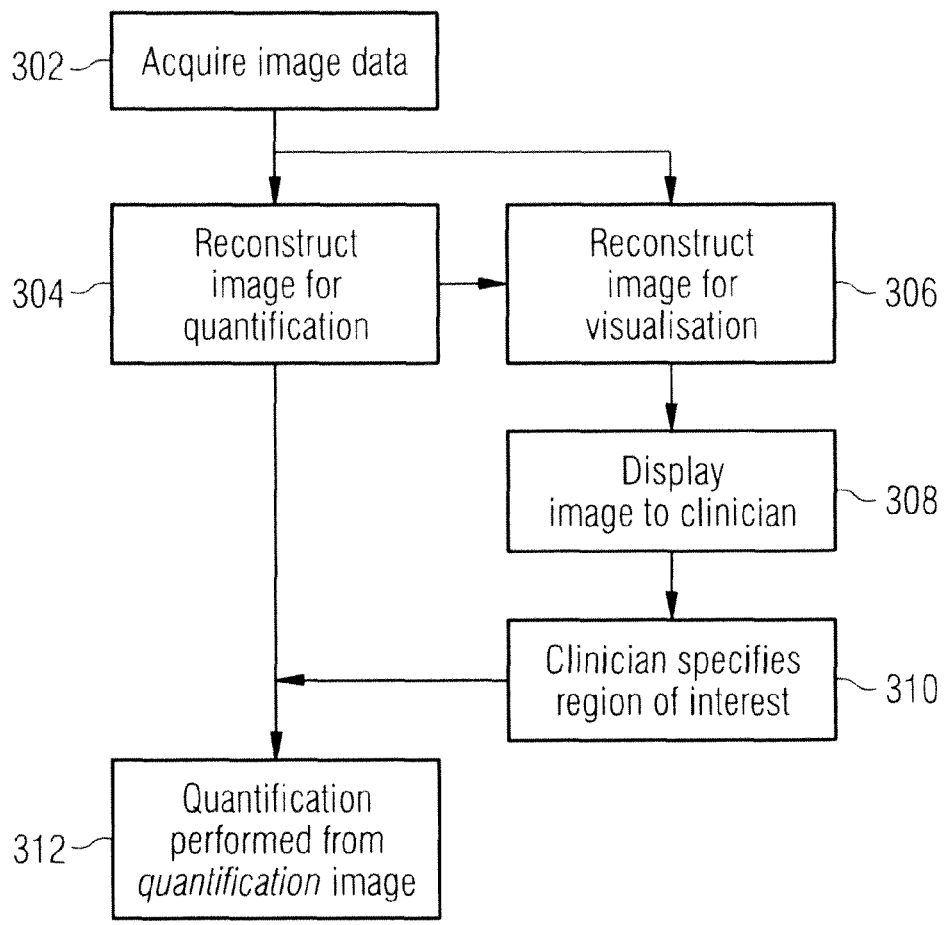
FIG. 3 is a flow diagram illustrating steps in a method according to an embodiment of the invention.

FIG. 3 is a flow diagram illustrating typical steps in an alternative method. The image is reconstructed for quantification only, by a specific reconstruction algorithm for this purpose (304), and is also fully reconstructed for visualization (306), providing two separate images. As an example, the image reconstructed for quantification (304) may have been generated with additional iterations of a reconstruction algorithm such as ordered subsets expectation maximization, when compared to the image reconstructed for visualization, resulting in a noisier but more converged image, allowing for greater accuracy for quantification. Similar steps as in FIG. 2 are taken, and the ROI specified by the clinician (310) is propagated to the specific quantification image (312) for retrieving, for example, mean SUV.

Therefore, in this embodiment, the method adapts the reconstruction itself specifically for quantification purposes and uses this image for quantification in addition to producing a conventionally reconstructed and filtered image. For example, it is known that running iterative reconstruction algorithms such as OSEM (Ordered Subset Expectation Maximization) for more iterations improves the accuracy of the any subsequent quantification. This does however increase the noise in the image. Therefore, producing two images at the reconstruction workstation, one for visual reading and the other for quantification will leverage the advantages of both images.

Embodiments of the invention may increase the amount of storage required for each scan. This may be mitigated in a number of ways. One approach is to not create and store the filtered image but instead perform any filtering at the reading workstation. This can be as the image is loaded, or real-time on display, in which case the smoothing can be done on-the-fly from the single non-filtered quantification image. In such case, there are never two copies of the whole image present—only the sections of the viewing image needed are filtered. To enable such a scheme to be backwards compatible with existing filtered data, a private tag in the DICOM header can be used to indicate whether the image requires a filter and to indicate the type and size of said filter. Exporting the image out of the proprietary system, say for example to PACS or CD/DVD, would require that the filter is applied.

Using this method, the recovery coefficients obtainable for the phantom lesions listed in Table 1 but derived from the unfiltered image are shown in Table 2.

TABLE 2

| Lesion diameter | Corrected recovery coefficient | Percentage improvement compared to original image |
| --- | --- | --- |
| 10 mm | 36.3% | 61.3% |
| 13 mm | 54.6% | 38.6% |
| 17 mm | 64.2% | 16.5% |
| 22 mm | 73.4% | 2.4% |

This table shows recovery coefficients for the same phantom acquisition presented in Table 1, generated using an embodiment of the PVC method described above. Improvement as a percentage of the original recovery coefficient is also provided.

Figure 4:
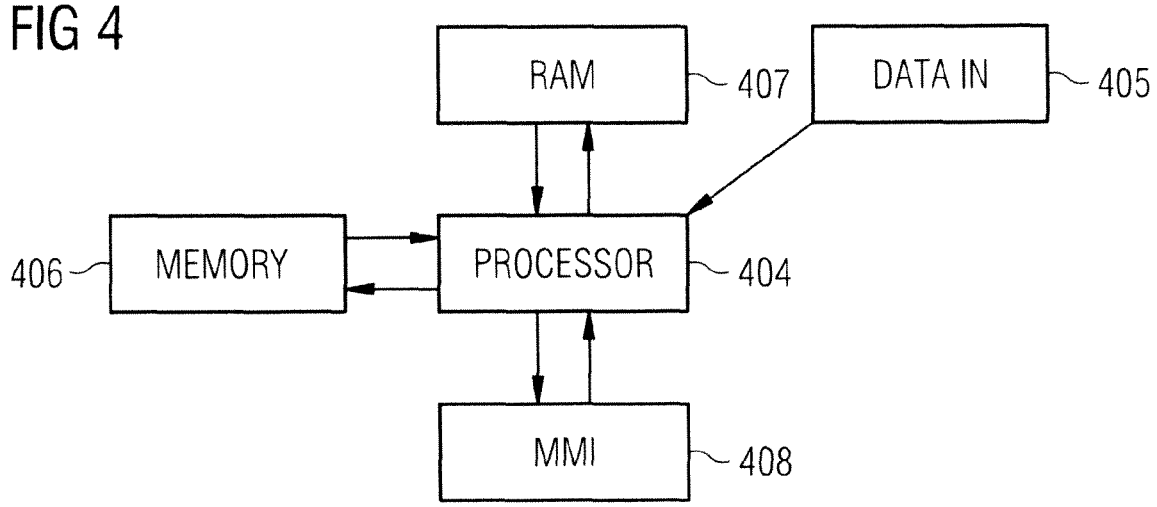
FIG. 4 is a diagram illustrating an apparatus according to an embodiment of the invention.

Referring to FIG. 4, the above embodiments of the invention may be conveniently realized as a computer system suitably programmed with instructions for carrying out the steps of the methods according to the invention.

For example, a central processing unit 404 is able to receive data representative of medical scans via a port 405 which could be a reader for portable data storage media (e.g. CD-ROM); a direct link with apparatus such as a medical scanner (not shown) or a connection to a network.

Software applications loaded on memory 406 are executed to process the image data in random access memory 407.

The processor 404 in conjunction with the software can perform the steps such as processing the image data to reconstruct a pre-image data set, applying the filter to the pre-image data set to produce the filtered image for display, and obtaining from the pre-image data set a value of a variable for display with the filtered image.

A Man-Machine interface 408 typically includes a keyboard/mouse/screen combination (which allows user input such as initiation of applications) and a screen on which the results of executing the applications are displayed.

It will be appreciated by those skilled in the art that the invention has been described by way of example only, and that a variety of alternative approaches may be adopted without departing from the scope of the invention, as defined by the appended claims.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method of generating an image for display from medical image data of a subject, comprising:
   processing the image data to reconstruct a pre-image data set; and
   applying a filter to the pre-image data set to produce a filtered image for display and displaying the filtered image to a user, using the pre-image data set as a quantification image and calculating at least one quantification parameter using data in the quantification image, and displaying a value of the at least one parameter to the user with the filtered image, or
   using the pre-image data set as a quantification image and calculating at least one quantification parameter using data in the quantification image, applying a filter to the pre-image data set to produce a filtered image for display and displaying the filtered image to a user, and displaying a value of the at least one parameter to the user with the filtered image.

2. The method according to claim 1 wherein the step of obtaining the value comprises:
   measuring at least one value of the parameter for a group of voxel data in the pre-image data set.

3. The method according to claim 1 wherein the step of obtaining the value comprises:
   identifying a user-selected region of interest in the filtered image;
   applying the region of interest to the quantification image and using that region of interest to calculate said at least one quantification parameter for use in displaying said value of the parameter.

4. The method of claim 3 wherein a group of voxel data is determined from the quantification image corresponding to said region of interest.

5. The method according to claim 4 comprising employing mean voxel intensity as said quantification parameter.

6. The method according to claim 3 further comprising setting a minimum size for the region of interest.

7. The method according to claim 1 further comprising applying the filter to the pre-image data set at a work station of said user.

8. The method according to claim 7 comprising applying the filter on demand for viewing by the user of the filtered image.

9. The method according to claim 7 further comprising before applying the filter, adding a tag to a header of the pre-image data set to indicate the requirement for a filter.

10. The method according to claim 1 comprising employing as said filter a smoothing post-filter for reducing image noise.

11. The method of claim 1 wherein said value is displayed to the user alongside said filtered image.

12. The method of claim 1 wherein said value is displayed to the user as an overlay on the filtered image.

13. An apparatus for generating an image on an image display from medical image data of a subject captured by an imaging apparatus, comprising:
   a processor configured to perform the steps of:
   processing the image data to reconstruct a pre-image data set; and
   applying a filter to the pre-image data set to produce a filtered image for display and displaying the filtered image to a user on said image display, using the pre-image data set as a quantification image and calculating at least one quantification parameter using data in the quantification image, and displaying a value of the at least one parameter to the user along with the filtered image on said display, or
   using the pre-image data set as a quantification image and calculating at least one quantification parameter using data in the quantification image, applying a filter to the pre-image data set to produce a filtered image for display and displaying the filtered image to a user on said display, and displaying a value of the at least one parameter to the user with the filtered image on said display.

14. A non-transitory computer-readable storage medium encoded with programming code, said storage medium being loadable into a computerized processor supplied with image data, and said programming code causing said processor to perform the steps of:
   processing the image data to reconstruct a pre-image data set; and
   applying a filter to the pre-image data set to produce a filtered image for display and displaying the filtered image to a user, using the pre-image data set as a quantification image and calculating at least one quantification parameter using data in the quantification image, and displaying a value of the at least one parameter to the user with the filtered image, or
   using the pre-image data set as a quantification image and calculating at least one quantification parameter using data in the quantification image, applying a filter to the pre-image data set to produce a filtered image for display and displaying the filtered image to a user, and displaying a value of the at least one parameter to the user with the filtered image.

* * * * *